United States Patent
Bear et al.

(10) Patent No.: US 10,100,273 B2
(45) Date of Patent: Oct. 16, 2018

(54) CLOSURE ASSEMBLY FOR CELL CULTURE APPARATUS

(75) Inventors: Adam J Bear, Gorham, ME (US); Heidi M Brown, Arundel, ME (US); Matthew D Mitchell, Wells Bridge, NY (US); James Philippe, Sanford, ME (US); Paul Kevin Seeto, Clinton, MA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/298,679

(22) Filed: Nov. 17, 2011

(65) Prior Publication Data

US 2012/0295343 A1 Nov. 22, 2012

Related U.S. Application Data

(60) Provisional application No. 61/415,970, filed on Nov. 22, 2010.

(51) Int. Cl.
  *C12M 1/00* (2006.01)
  *C12M 1/24* (2006.01)
  *B65D 51/00* (2006.01)

(52) U.S. Cl.
  CPC .......... *C12M 23/38* (2013.01); *B65D 51/002* (2013.01); *C12M 23/08* (2013.01)

(58) Field of Classification Search
  USPC ........ 435/289.1, 283.1–309.4; 215/252, 342, 215/352
  See application file for complete search history.

(56) References Cited

U.S. PATENT DOCUMENTS

| | | | |
|---|---|---|---|
| 3,499,568 A | 3/1970 | Riera | |
| 3,679,084 A * | 7/1972 | Aronson | B65D 50/048 215/217 |
| 3,709,395 A | 1/1973 | Brennan et al. | |
| 3,827,592 A * | 8/1974 | Deussen | B65D 50/067 215/215 |
| 3,904,059 A | 9/1975 | Bellamy, Jr. et al. | |

(Continued)

FOREIGN PATENT DOCUMENTS

| DE | 2536097 | 3/1977 |
|---|---|---|
| FR | 2444081 | 7/1980 |

OTHER PUBLICATIONS

JP2013-540976 Office action dated Jun. 1, 2015.
EP17166452 Suppplementary Search Report Completed Jun. 29, 2017; European Patent Office; 3 Pages.

*Primary Examiner* — Jonathan M Hurst
(74) *Attorney, Agent, or Firm* — John P. Ciccarelli

(57) ABSTRACT

A closure assembly for a cell culture apparatus includes a port and a snap cap. The port has an annular sidewall defining an opening in communication with a cell culture chamber of a cell culture apparatus. The sidewall has (i) external threads for cooperating with internal threads of a twist cap and (ii) an annularly protruding snap cap engagement feature. The snap cap has a top and an annular sidewall extending from the top. The sidewall of the snap cap has an inwardly annularly projecting element configured to engage with the annularly protruding snap cap engagement feature of the port such that, when fully engaged, the snap cap is not readily removed from the port by unaided human force.

4 Claims, 8 Drawing Sheets

(56) References Cited

U.S. PATENT DOCUMENTS

| | | | |
|---|---|---|---|
| 3,910,444 A * | 10/1975 | Foster | 215/295 |
| 3,971,487 A | 7/1976 | Montgomery | |
| 4,334,028 A * | 6/1982 | Carver | C12M 23/32 |
| | | | 215/228 |
| 4,763,804 A | 8/1988 | O'Connell | |
| 4,872,304 A * | 10/1989 | Thompson | 53/487 |
| 4,993,573 A | 2/1991 | Freidel et al. | |
| 5,165,559 A | 11/1992 | Kusz | |
| 5,699,923 A * | 12/1997 | Burns | B01L 3/50825 |
| | | | 215/247 |
| 5,813,553 A * | 9/1998 | Herr | B65D 41/3438 |
| | | | 215/252 |
| 2001/0000602 A1* | 5/2001 | Luch | 215/256 |
| 2006/0231519 A1* | 10/2006 | Py | B65D 51/002 |
| | | | 215/342 |
| 2007/0166822 A1* | 7/2007 | Kenney | C12M 23/08 |
| | | | 435/325 |
| 2008/0044603 A1* | 2/2008 | Hutchinson et al. | 428/35.7 |
| 2008/0164235 A1* | 7/2008 | Ekkert | 215/352 |
| 2008/0169262 A1 | 7/2008 | Ekkert | |
| 2008/0227176 A1* | 9/2008 | Wilson | C12M 23/08 |
| | | | 435/243 |

\* cited by examiner

CLOSURE ASSEMBLY FOR CELL CULTURE APPARATUS

CROSS-REFERENCE TO RELATED APPLICATIONS

This application claims the benefit of priority under 35 U.S.C. § 119 of U.S. Provisional Application Ser. No. 61/415,970 filed on Nov. 22, 2010 the content of which is relied upon and incorporated herein by reference in its entirety.

FIELD

The present disclosure relates to cell culture apparatuses, and more particularly to ports and closure assemblies for such apparatuses.

BACKGROUND

Cell culture apparatuses have ports for introducing cells, culture media, or other fluids into cell culture chambers. Often, caps are used to seal the ports when fluids or cells are not being introduced to prevent contamination of the cell culture chamber. In many instances the caps are threaded and may engage external threads on the port to twist the cap onto the port. An advantage of such twist caps is that they can be readily removed to access the cell chamber port. At early stages of research or development it is often desirable to repeatedly twist on and twist off the cap to obtain samples from the culture chamber or introduce agents or fluid into the culture chamber.

However, at later stages of development or validation for purposes of regulatory approval, it is often desired or required that the culture chamber be closed or sealed. While twist caps can be used for such purposes, it is often difficult to ensure that the cap is properly seated; e.g., not canted, or that the cap will not accidentally be removed.

Accordingly, different culture apparatuses are often employed for purposes of early research or development and later stages of development or validation. The earlier stages employing a device with a readily removable cap, and the later stages employing a device with a less easily removable cap. However, switching culture apparatuses during these stages is often undesirable, as the results obtained in the first culture apparatus may not be repeatedly observed in a second different culture apparatus.

BRIEF SUMMARY

The present disclosure describes, among other things, a cell culture apparatus having a port configured to engage either a twist cap or a snap cap. In many embodiments, the port and twist cap are configured to allow easy removal and attachment of the cap relative to the port. In contrast, the snap cap and port are configured such that the snap cap cannot readily, if at all, be removed from the port by unaided human force once the snap cap is fully engaged with the port. By configuring the port to engage a removable cap and an irremovable cap, the same culture device may be used for purposes of early research in which opening and closing of the system may be desirable and more rigorous validation in which a permanently closed system is desired or required.

In various embodiments described herein, a cell culture apparatus includes a cell culture chamber and a port having an annular sidewall defining an opening in communication with the cell culture chamber. The annular sidewall of the port has (i) external threads configured to cooperate with internal threads of a twist cap and (ii) an annularly protruding snap cap engagement feature configured to cooperate with a snap cap. The engagement feature has a top surface and a bottom surface configured to engage a feature of a snap cap to resist the snap cap from being pulled off the port. The bottom surface of the engagement feature extends from the sidewall of the port at an angle of less than 110 degrees.

In numerous embodiments described herein, a closure assembly for a cell culture apparatus includes a port and a snap cap. The port has an annular sidewall defining an opening in communication with a cell culture chamber of the cell culture apparatus. The sidewall has (i) external threads for cooperating with internal threads of a twist cap and (ii) an annularly protruding snap cap engagement feature. The snap cap has a top and an annular sidewall extending from the top. The sidewall of the snap cap has an inwardly annularly projecting element configured to engage with the annularly protruding snap cap engagement feature of the port such that when fully engaged, the snap cap is not readily removed from the port by unaided human force. The annularly protruding snap cap engagement feature of the port may have a top surface and a bottom, wherein the bottom surface of the engagement feature extends from the sidewall of the port at an angle of less than 110 degrees. The inwardly annularly projecting element of the snap cap may have a top surface and a bottom surface, wherein the top surface of the inwardly annularly projecting element of the snap cap is configured to engage with bottom surface of the engagement feature of the port when a pulling force is applied to the cap. The top surface of the inwardly annularly projecting element of the snap cap may extend from the surface of the sidewall at an angle of less than 110 degrees.

The closure assembly may further include a stopper having a proximal end portion configured to be received by the opening of the port and a distal end portion configured to remain external to the port. The distal end portion has a flange with an outer diameter greater than the inner diameter of the sidewall of the port at the opening. A bottom surface of the top of the snap cap, when the snap cap is fully engaged with the port, is configured to compress the flange of the stopper against the top of the port. In some embodiments, this may also force the stopper against the sidewall of the port.

The assemblies, devices, articles and methods described herein may provide one or more advantages over prior cell culture systems. For example, being able to use a single cell culture apparatus for early research and development with a readily removable cap and to use the same device for later stage validation with a different cap that is not readily removable can result in potential anomalous results associated with use of different culture apparatuses for such purposes. This and other advantages of the various embodiments of the assemblies, devices, articles and methods described herein will be readily apparent to those of skill in the art upon reading the disclosure presented herein.

Figure 1:
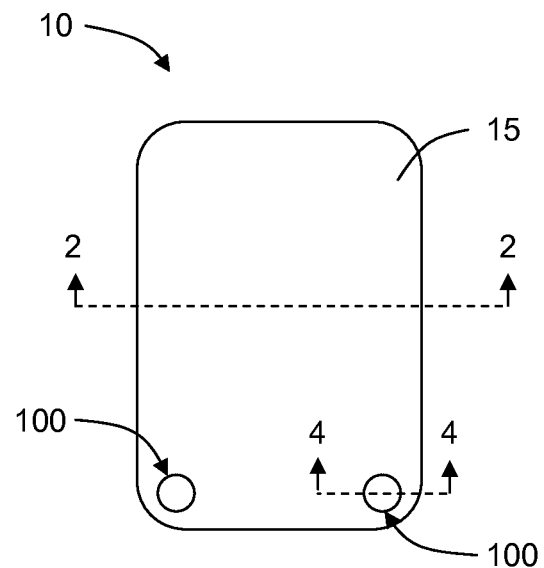
FIG. 1 is a schematic top view of an example of a cell culture apparatus.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like. For example, a closure assembly for a cell culture apparatus comprising a port, a cap, and a stopper may consist of, or consist essentially of, the port, the cap and the stopper.

"Consisting essentially of", as it relates to a compositions, articles, systems, apparatuses or methods, means that the compositions, articles, systems, apparatuses or methods include only the recited components or steps of the compositions, articles, systems, apparatuses or methods and, optionally, other components or steps that do not materially affect the basic and novel properties of the compositions, articles, systems, apparatuses or methods.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations.

The present disclosure describes, among other things, a cell culture apparatus having a port configured to engage either a twist cap or a snap cap. In many embodiments, the port and twist cap are configured to allow easy removal and attachment of the cap relative to the port, while the snap cap and port are configured such that the snap cap cannot readily, if at all, be removed from the port by unaided human force once the snap cap is fully engaged with the port. By configuring the port to engage a removable cap and a relatively irremovable cap, the same culture device may be used for purposes of early research in which opening and closing of the system may be desirable and more rigorous validation in which a permanently closed system is desired or required.

The closure assemblies described herein may be used in any suitable cell culture system. For example, jars, flasks, bottles, plates, beakers, tubes, bags, perfusion chambers, bioreactors, Corning Incorporated's CellSTACK® culture chamber devices, and fermenters may be readily adapted to incorporate a closure assembly or components thereof.

By way of example and referring to FIG. 1, a schematic top view of an example of a cell culture apparatus 10 that incorporates a port 100, as described herein, is shown. The depicted cell culture apparatus 10 has a top surface 15 and two ports 100 extending from the top surface. While two ports are shown, it will be understood that a cell culture apparatus 10 may include any suitable number of ports 100. It will also be understood that while the ports 100 are depicted as extending from a top surface 15 of the apparatus 10, one or more ports 100 may be positioned at any suitable location of the apparatus 10 to provide access to an interior chamber of the apparatus.

Figure 2:
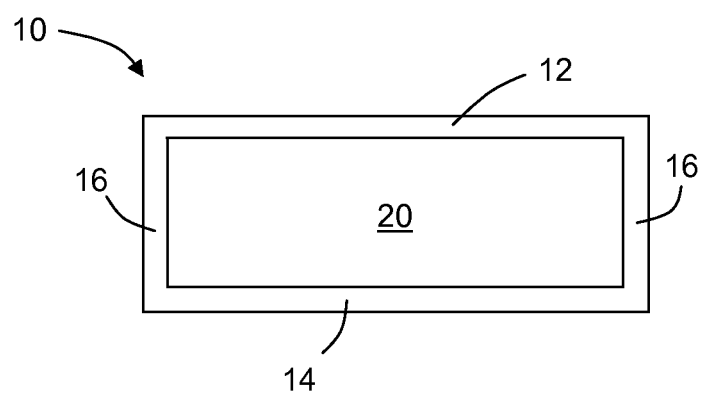
FIG. 2 is a schematic cross sectional view of an embodiment of the apparatus depicted in FIG. 1, taken through line 2-2.

Referring now to FIG. 2, a schematic cross-sectional view, taken through line 2-2 of an embodiment of a cell culture apparatus of FIG. 1, is shown. The depicted apparatus 10 includes a cell culture chamber 20 defined by top 12, bottom 14, and side 16 walls. The top wall 12 of the culture chamber 20 also serves as the top of the apparatus in the depicted embodiment. One or more port 100 (see, e.g., FIG. 1) is in communication with the chamber 20 to provide access to the chamber. Of course, the apparatus 10 depicted in FIG. 2 is a fairly simple apparatus, it will be understood that more complex apparatuses, such as those having multiple cell culture chambers, tracheal chambers, or chambers for introducing fluids adjacent cell culture chambers, may be modified to include a port or closure assembly as described herein. In any case, a port described herein provides access to one or more chamber of a cell culture apparatus.

Figure 3:
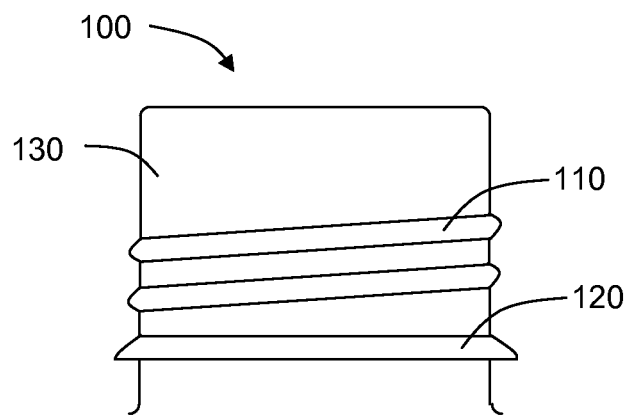
FIG. 3 is a schematic side view of a port of a cell culture apparatus.
Figure 4:
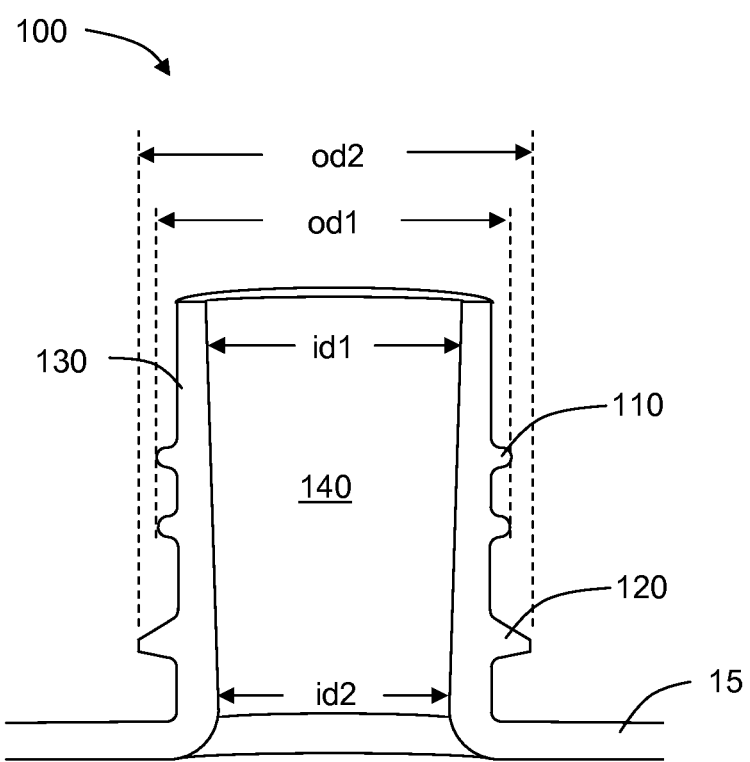
FIG. 4 is a schematic cross sectional view of an embodiment of a port of the apparatus depicted in FIG. 1, taken through line 4-4.

Referring now to FIGS. 3-4, schematic side and cross sectional views of an embodiment of a cell culture apparatus port 100 configured to engage a twist cap or a snap on cap is depicted. The port 100 has an annular side wall 130 with exterior threads 110 configured to engage and cooperate with internal threads of a twist cap. An annularly protruding snap cap engagement feature 120 extends from the sidewall 130 and is configured to engage and cooperate with a snap-on cap. In the embodiment depicted in FIGS. 3-4, the snap cap engagement feature 120 is positioned more proximal to the surface 15 of the cell culture apparatus than the threads 110. In addition, the largest outer diameter (od2) of the annularly protruding snap cap engagement feature 120 is greater than the largest outer diameter (od1) of the external threads 110. This allows a cooperating engagement element of a snap cap to be advanced over the threads 110 without the threads interfering with advancement of the snap cap, as will be discussed further with regard to FIG. 10 below.

In the embodiment depicted in FIG. 4, the annular sidewall 130 of the port 100 defines a lumen 140 that is in communication with the exterior of the port and one or more chambers of the culture apparatus. The depicted lumen 140 is tapered such that it has a larger inner diameter (id1) closer to the external opening of the port and a smaller inner diameter (id2) closer to the cell culture apparatus. Such tapering may provide for improved sealing engagement between a stopper and the internal surface of the sidewalls 130 of the port 100 when use of a stopper is desired. Of course, many suitable stoppers may be employed with ports that do not have such tapered inner sidewalls.

Figure 5:
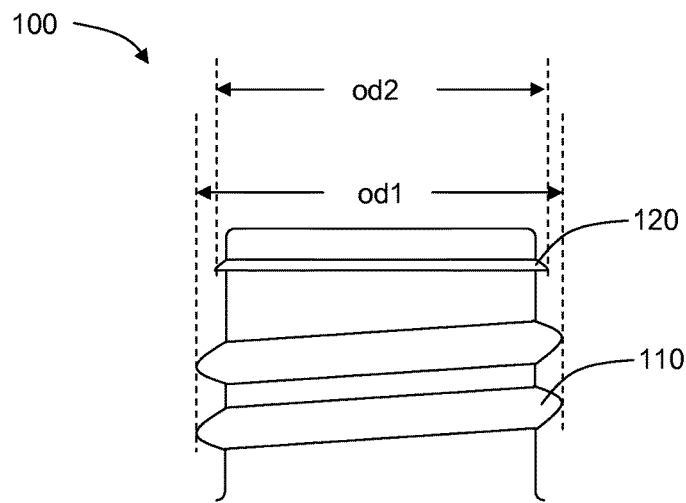
FIG. 5 is a schematic side view of a port of a cell culture apparatus.

Referring now to FIG. 5, a schematic side view of an embodiment of a cell culture apparatus port 100 configured to engage a twist cap or a snap on cap is depicted. In the depicted embodiment, the exterior threads 110, which are configured to engage and cooperate with internal threads of a twist cap, are positioned more proximal to a surface of the cell culture apparatus than the snap cap engagement feature 120, which is configured to engage and cooperate with a snap-on cap. In this embodiment, the largest outer diameter (od2) of the annularly protruding snap cap engagement feature 120 is less than the largest outer diameter (od1) of the external threads 110. This allows internal threads of a twist cap, which are configured to cooperate and engage with external threads 110, to be advanced over the snap cap engagement feature 120 without the feature 120 interfering with advancement of the twist cap about the port 100. Of course, the threads 110 and the snap cap engagement feature 120 may be placed in any suitable position relative to each other that provides that a snap cap can properly engage the feature 120 and a twist cap can properly engage the threads 110.

Figure 6A:
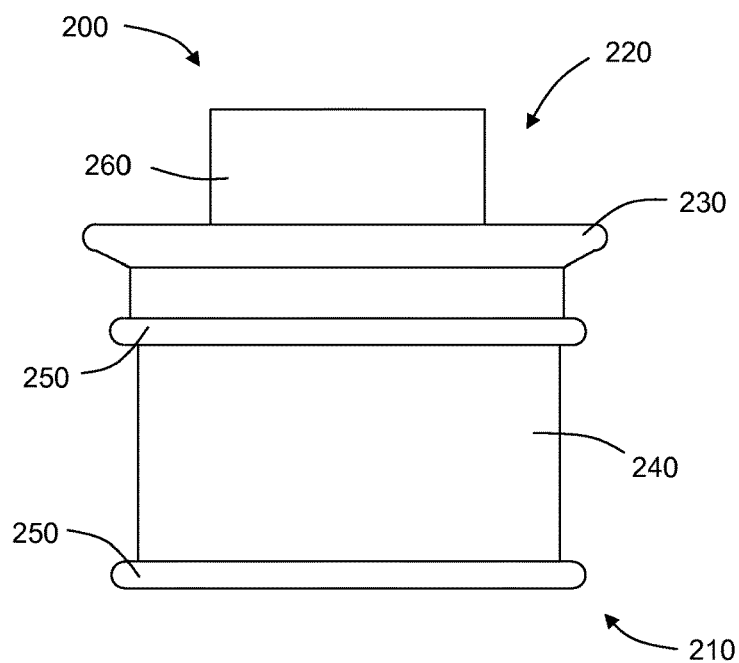
FIGS. 6A and 6B are schematic side and top views of an embodiment of a stopper that may be at least partially inserted into a port of a cell culture apparatus.
Figure 6B:
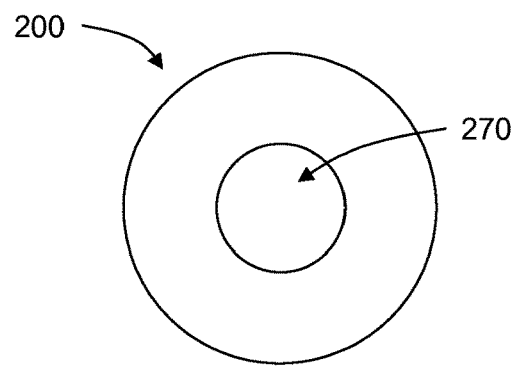

Referring now to FIGS. 6A, 6B, a schematic side and top views of an embodiment of a stopper 200 that may be used with a closure assembly described herein. The stopper 200 is configured to be received by and sealingly engage a port of a cell culture apparatus. The depicted stopper 200 has a proximal end portion 210 configured to be received by a lumen of a port, and a distal end portion 220 configured to remain external to the port. The proximal end portion 210 may include one or more annular ring 250 (two depicted) extending outwardly from the body 240 of the stopper 200. The annular rings 250 are configured to sealingly engage an inner surface of the annular sidewall of the port.

The distal end portion 220 of the depicted stopper 200 includes an annular flange 230 radially extending from the body 240 of the stopper. The bottom surface of the flange 230 is configured to sealingly engage a top surface of the port. Accordingly, the outer diameter of the flange 230 is larger than the inner diameter of the annular sidewall of the port at the exterior opening of the port. A bottom surface of a cap, such as a snap cap (e.g., as described further below with regard to FIG. 11), may be configured to press the flange against the top surface of the port when the cap is fully engaged with the port.

The distal end portion 220 of the stopper 200 depicted in the embodiment shown in FIG. 6A includes a distal extension 260 defining a lumen 270 (see FIG. 6B) configured to sealing receive tubing for introducing gas or fluids into the culture apparatus through the port when the stopper 200 is sealingly engaged with the port. Any suitable tubing, such as glass tubing, metal tubing or plastic tubing may be employed for this purpose.

Figure 7:
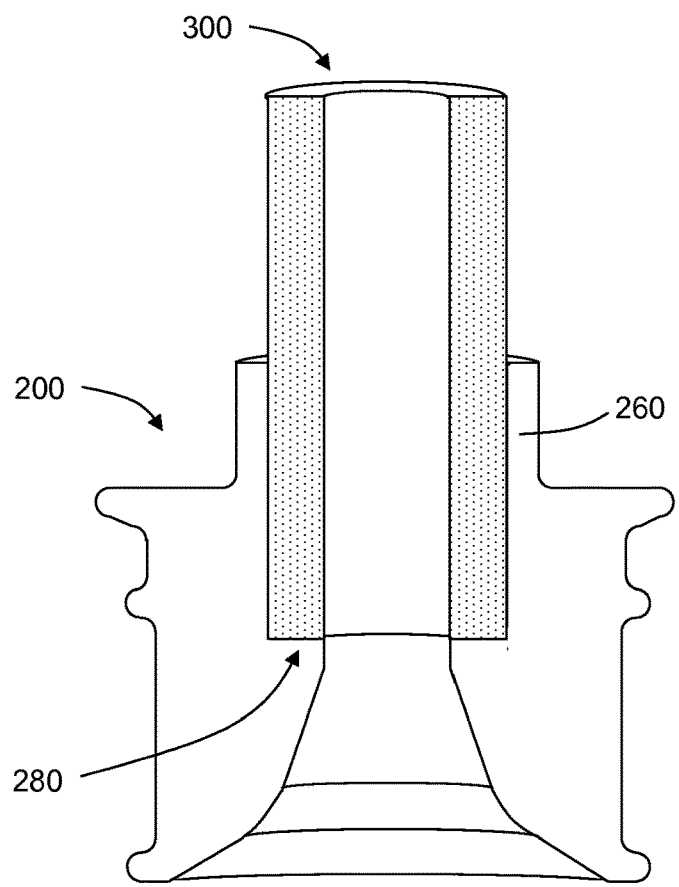
FIG. 7 is a schematic cross sectional view of an embodiment of a stopper and tubing received by a lumen of the stopper.

Referring now to FIG. 7, a schematic cross sectional view of an embodiment of the stopper 200 depicted in FIGS. 6A and 6B is shown. In FIG. 7, tubing 300 is shown inserted into the lumen 270 (see FIG. 6B) defined by the distal extension 260 of the stopper 200. In the depicted embodiment, an interior portion of the stopper 200 forms an annular shoulder projecting into the lumen to prevent further proximal insertion of the tubing 300 into the stopper 200. The tubing 300 may be inserted into the stopper 200 by an end used of a cell culture apparatus or may be pre-inserted by a manufacturer. Frictional forces may hold the tubing 300 relative to the stopper 200 or the tubing may be adhered, welded or otherwise affixed to the stopper 200. In some embodiments, the tubing 300 is molded as part of the stopper 200, reducing a potential leak point between the stopper 200 and the tubing 300. In the embodiment depicted in FIG. 7, the internal shape of the stopper 300 is designed to reduce fluid hang-up around the area of the stopper 200 and port 100, allowing for complete, or near complete, fluid removal.

Figure 8:
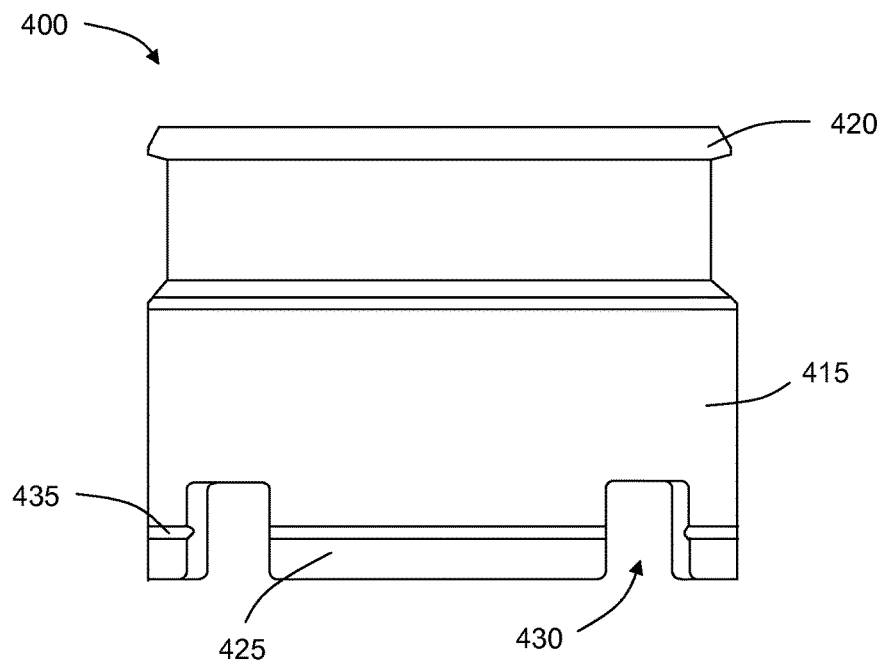
FIG. 8 is a schematic side view of an embodiment of a snap-on cap configured to engage a port of a cell culture apparatus.
Figure 9:
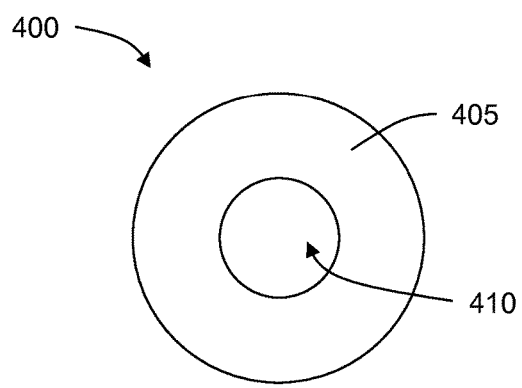
FIG. 9 is a schematic top view of an embodiment of the snap-on cap depicted in FIG. 8.
Figure 10:
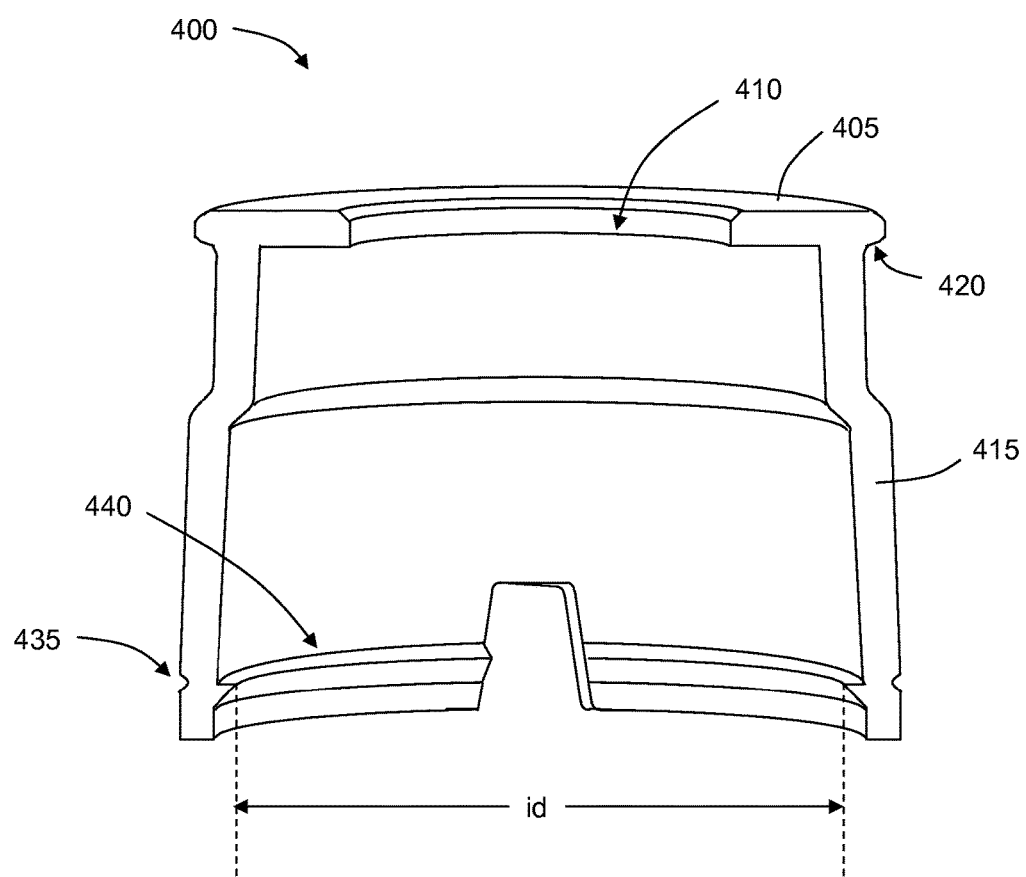
FIG. 10 is a schematic cross sectional view of an embodiment of the cap depicted in FIG. 8.

Referring now to FIGS. 8-10, schematic side, top and cross sectional views of an embodiment of a snap on cap 400 are depicted. The depicted snap cap has a top 405 defining an opening 410 through which a distal extension of a stopper may project. The cap 400 includes an annular sidewall 415 or skirt extending from the top 405. One or more gaps 430 are incorporated into the sidewall 415 at an end distal to the top 405 of the cap. An extension 425 is formed between adjacent gaps 430. The extensions 425 are resiliently and radially outwardly deflectable. An annularly projecting element 440 extends inwardly from the sidewall 415, in the depicted case from the sidewall extensions 425. As will be discussed in more detail below with regard to FIGS. 11-12, the inwardly annularly projecting element 440 cooperates with the snap cap engagement feature of the port. Preferably, when the snap cap 400 is fully engaged with the port, the cap 400 cannot be removed by unaided human force. That is, the snap cap 400 serves as a permanent cap to provide a permanently sealed cell culture apparatus.

In various embodiments, the snap cap and port are configured such that the snap cap cannot be removed from the port with a pull force of less than 50, 75, 100, 125 or 150 pounds. In some embodiments, the snap cap and port are configured such that the snap cap cannot be pulled off of the port without breaking the snap cap or port or a portion thereof.

The snap cap 400 may include a flange 420, in the depicted embodiment—coextensive with the top 405, that may be used for purposes of providing a surface against which to pull the cap 400 to determine if the cap is fully engaged with the port (i.e., has properly snapped into place about the port). In addition, the snap cap 400 may include an annular detent 435 that extends around the exterior of the sidewall 415 (in this case the side wall extensions 425) equidistant the top 405 as the inwardly annularly projecting element 440. The detent 435 or other suitable marking, in combination with the gaps 430, may be used to visually verify that the inwardly annularly projecting element 440 is properly engaged with the snap cap engagement feature of the port (e.g. to verify that the snap cap is fully engaged and not canted).

The inwardly annularly projecting element 440 depicted in FIG. 10 defines an inner diameter (id) that is greater than the outer diameter of the external threads of the port so that the cap 400 may be advanced over the port without the external threads interfering with the advancement of the cap. In some embodiment (not shown), the snap cap may also include internal threads configured to cooperate with the external threads of the port so that the snap cap may be twisted until the snap elements of the cap and port are engaged. However, in some situations it may be desirable to omit such internal threads, as canting can often be a problem with such twist on mechanisms.

Figure 11:
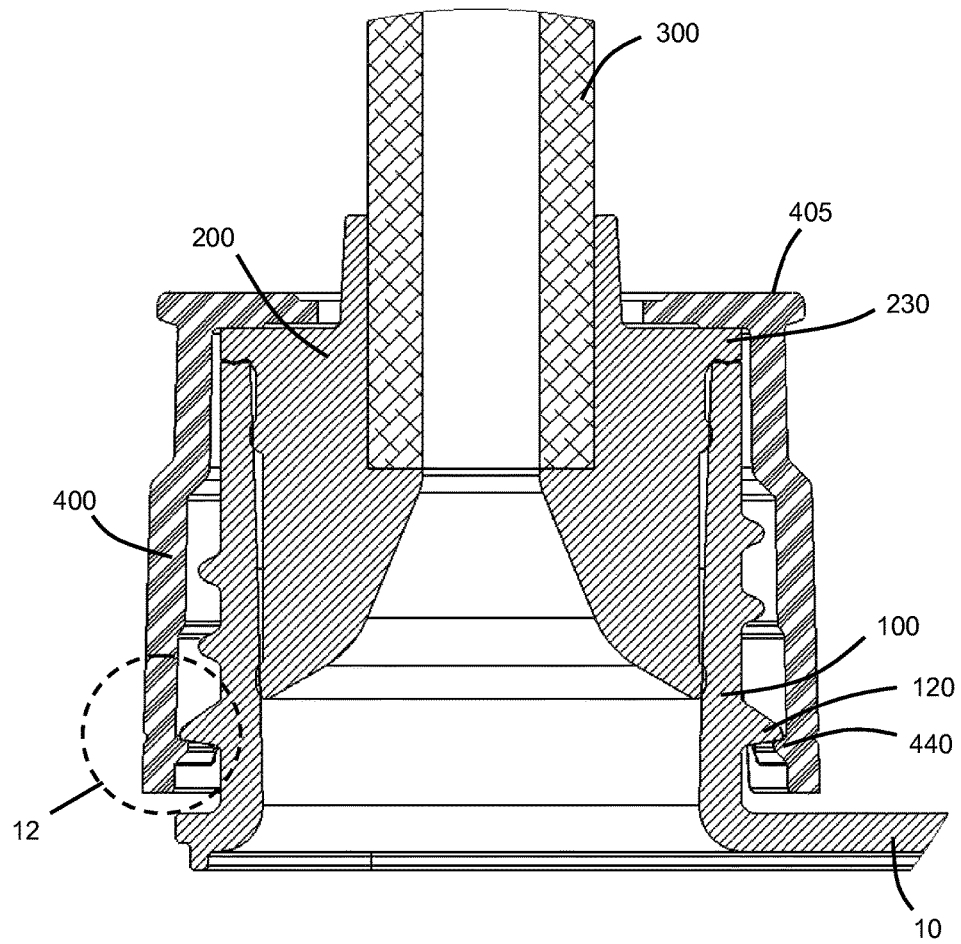
FIG. 11 is a schematic cross sectional view of a closure assembly of a cell culture device showing a port, a stopper, a snap-on cap, and tubing.

Referring now to FIG. 11, a schematic cross sectional view of a closure assembly of a cell culture apparatus is shown, with like numbers referring to like components described with regard to, and depicted in, FIGS. 1-10. The depicted assembly includes (i) a port 100 attached to, integrally formed with, or otherwise affixed to a cell culture apparatus 10, (ii) a stopper 200 received in, and sealingly engaged with, a lumen of the port 400, (iii) tubing 300 received in, and sealingly engaged with, a lumen of the stopper 200, and (iv) a cap 400 fully engaged with the port 100. When the cap 400 is fully engaged with the port 100, a bottom surface of the top 405 of the cap engages with and compresses the flange 230 of the stopper 200 against a top surface of the port 100 to form a fluid seal and also forces the stopper against the sidewall of the port. In embodiments, where it may be desirable to seal a port 100 without providing access to the port via tubing 300, the top 405 of the cap may be solid (without an opening), and a gasket or other compressible material may be substituted for the flange of the stopper to provide a fluid seal.

As shown in FIG. 11, the annularly protruding snap cap engagement feature 120 of the port 100 and the inwardly annularly projecting element 440 of the cap cooperate to prevent the cap 400 from being pulled off the port 100.

Figure 12:
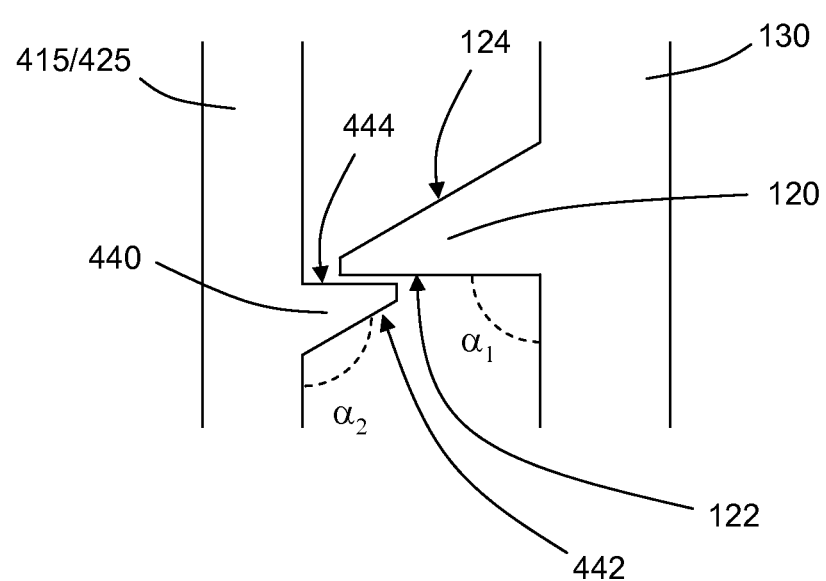
FIG. 12 is a schematic close up view of cooperating engagement features of a snap-on cap and a port showing the cap fully placed on and engaged with the port.

Additional details of an embodiment of the annularly protruding snap cap engagement feature 120 of the port and the inwardly annularly projecting element 440 of the cap are shown in FIG. 12. In the depicted embodiment, the annularly protruding snap cap engagement feature 120 of the port has a bottom surface 122 and top surface 124 extending from the sidewall 130 of the port. For purposes of this disclosure, the top surface 124 is the surface facing generally away from a surface of the cell culture apparatus (e.g., surface 15 of FIG. 4) and the bottom surface 122 is the surface generally facing the surface of the cell culture apparatus.

The inwardly annularly projecting element 440 of the snap cap has a bottom surface 442 and top surface 444 extending from the sidewall 425 of the cap. For purposes of this disclosure, the bottom surface 442 is the surface generally facing the opening of the cap that is configured to be advanced over the port, and the top surface 444 is the surface facing generally from the opening of the cap.

Still referring to FIG. 12, the bottom surface of the 112 of the annularly protruding snap cap engagement feature 120 of the port extends from the port sidewall 130 at an angle ($\alpha_1$). The inwardly annularly projecting element 440 of the snap cap extends from the cap side wall 425 at an angle of about $\alpha_1$. To provide an interaction between the inwardly annularly projecting element 440 of the snap cap and the annularly protruding snap cap engagement feature 120 of the port that will prevent the cap from being pulled off the port, $\alpha_1$ is 90±20 degrees (i.e., between 70 and 110 degrees, such as between 100 and 80 degrees).

The bottom surface 442 of the inwardly annularly projecting element 440 of the snap cap and the top surface 124 of the annularly protruding snap cap engagement feature 120 of the port cooperate to facilitate placement and full engagement of the cap about the port. As the cap is pressed down relative to the port, the ramped bottom surface 442 of the inwardly annularly projecting element 440 of the cap engages the ramped top surface 124 of the annularly protruding snap cap engagement feature 120 of the port, causing the sidewall extension 425 to deflect radially outward. Once the cap is pushed a sufficient distance relative to the port, the sidewall extension 425 resumes its relaxed configuration and the annularly projecting element 440 of the cap clears the annularly protruding snap cap engagement feature 120 of the port (i.e., in the fully engaged configuration depicted in FIG. 12). To aid in the movement of the cap into the fully engaged position relative to the port, the bottom surface 442 of the inwardly annularly projecting element 440 of the cap extends from the cap sidewall 415 at an angle ($\alpha_2$) of 135±15 degrees (i.e., between 120 and 150 degrees, such as between 130 and 140 degrees). The top surface 124 of the annularly protruding snap cap engagement feature 120 of the port extends from the port sidewall 130 at an angle of about $\alpha_2$.

Of course the top and bottom surfaces of the cooperating snap features of the cap and port may be configured in any other suitable manner to facilitate placement and engagement of the cap relative to the port. For example, the surfaces may be rounded, polished or coated to facilitate placement. By way of further example, the surfaces may be roughened, contain latches and catches or other cooperating features to facilitate full engagement (and thus prevention or inhibition of removal of the cap from the port).

A port as described herein may be made from any suitable material, such as a hard plastic material, glass, metal or the like. Examples of suitable plastic materials include high density polyethylene (HDPE), polypropylene, polycarbonate, polystyrene and the like. Preferably the port is formed from biocompatible material. In some embodiments, the port is formed from the same or similar material as the housing of the cell culture apparatus. The port may be integrally molded with a portion of the housing of the cell culture apparatus, may be welded, adhered, or otherwise affixed to the cell culture apparatus.

A stopper as described herein may be made of any suitable material, such as rubber material. Examples of suitable rubber materials include butyl rubber, silicone rubber, and the like. Preferably, the stopper is formed from a biocompatible material. A stopper may be formed by any suitable process, such as molding. In some embodiments, the annular rings or flange of the stopper are made of a suitable rubber material, while the body is formed from another material such as a harder plastic material.

A cap as described herein may be made from any suitable material, such as a hard plastic material, metal or the like. Examples of suitable plastic materials include high density polyethylene (HDPE), polypropylene, polycarbonate, and the like. Preferably the cap is formed from biocompatible material. In some embodiments, the cap is formed from the same or similar material as the port. The cap may be formed by any suitable process, such as molding.

This disclosure in various aspects describes articles, assemblies and methods.

In a first aspect a cell culture apparatus is described. The cell culture apparatus comprises a cell culture chamber and a port. The port has an annular sidewall defining an opening in communication with the cell culture chamber. The sidewall comprises (i) external threads configured to cooperate with internal threads of a twist cap and (ii) an annularly protruding snap cap engagement feature. The engagement feature has a top surface and a bottom surface configured to engage a feature of a snap cap to resist the snap cap from being pulled off the port. The bottom surface of the engagement feature extends from the side wall at an angle of less than 110 degrees.

A second aspect is a cell culture apparatus of the first aspect, wherein the bottom surface of the engagement feature extends from the side wall at an angle of between 105 degrees and 75 degrees.

A third aspect is a cell culture apparatus of the first aspect, wherein the bottom surface of the engagement feature extends from the side wall at an angle of between 100 degrees and 80 degrees.

A fourth aspect is a cell culture apparatus of any of the first three aspects, wherein the top surface of the engagement feature extends from the sidewall at an angle between 120 and 150 degrees.

A fifth aspect is a cell culture apparatus of any of the first three aspects, wherein the top surface of the engagement feature extends from the sidewall at an angle between 130 and 140 degrees.

A sixth aspect is a cell culture apparatus of any of the first five aspects, wherein the annularly protruding snap cap engagement feature defines a largest outer diameter greater than the largest outer diameter defined by the external threads.

A seventh aspect is a cell culture apparatus of the sixth aspect, wherein the annularly protruding snap cap engagement feature is positioned along the sidewall at a location more proximal to the cell culture chamber than the external threads.

An eighth aspect is a closure assembly for a cell culture apparatus. The closure assembly comprises a port and a snap cap. The port has an annular sidewall defining an opening in communication with a cell culture chamber of the cell culture apparatus, wherein the sidewall comprises (i) external threads for cooperating with internal threads of a twist cap and (ii) an annularly protruding snap cap engagement feature. The snap cap has a top and an annular sidewall extending from the top, wherein the sidewall of the snap cap comprises an inwardly annularly projecting element configured to engage with the annularly protruding snap cap engagement feature of the port such that when fully engaged, the snap cap is not readily removed from the port by unaided human force.

A ninth aspect is a closure assembly of the eighth aspect, wherein the snap cap and port are configured such that the snap cap cannot be removed from the port with a pull force of less than 75 pounds.

A tenth aspect is a closure assembly of the eighth aspect, wherein the snap cap and port are configured such that the snap cap cannot be removed from the port by pulling on the cap in a direction along the axis of the opening of the port without breaking the annularly protruding snap cap engagement feature of the port or the inwardly annularly projecting element of the snap cap.

An eleventh aspect is a closure assembly of any of aspects 8-10, wherein the annularly protruding snap cap engagement feature of the port has a top surface and a bottom surface, wherein the bottom surface of the engagement feature extends from the sidewall of the port at an angle of less than 110 degrees, and wherein the inwardly annularly projecting element of the snap cap has a top surface and a bottom surface, wherein the top surface of the inwardly annularly projecting element of the snap cap is configured to engage with bottom surface of the engagement feature of the port when a pulling force is applied to the cap, and wherein the top surface of the inwardly annularly projecting element of the snap cap extends from the surface of the sidewall at an angle of less than 110 degrees.

A twelfth aspect is a closure assembly of the eleventh aspect, wherein the bottom surface of the engagement feature of the port extends from the side wall of the port at an angle of between 100 degrees and 80 degrees, and wherein the top surface of the inwardly annularly projecting element of the snap cap extends from the surface of the sidewall at an angle of between 100 degrees and 80 degrees.

A thirteenth aspect is a closure assembly of any of aspects 8-11, wherein the top surface of the engagement feature extends from the sidewall at an angle between 120 and 150 degrees, and wherein the bottom surface of the inwardly annularly projecting element of the snap cap extends from the surface of the sidewall at an angle of between 120 and 150 degrees.

A fourteenth aspect is a closure assembly of any of aspects 8-13, wherein the annularly protruding snap cap engagement feature of the port defines a largest outer diameter greater than the largest outer diameter defined by the external threads of the port.

A fifteenth aspect is a closure assembly of the fourteenth aspect, wherein the annularly protruding snap cap engagement feature is positioned along the sidewall at a location more proximal to the cell culture chamber than the external threads.

A sixteenth aspect is a closure assembly of any of aspects 8-15, further comprising a stopper having a proximal end portion configured to be received by the opening of the port and a distal end portion configured to remain external to the port, the distal end portion comprising a flange having an outer diameter greater than the inner diameter of the sidewall of the port at the opening, wherein a bottom surface of the top of the snap cap, when the snap cap is fully engaged with the port, is configured to compress the flange of the stopper against the top of the port. In some embodiments, this may also force the stopper against the sidewall of the port.

A seventeenth aspect is a closure assembly of the sixteenth aspect, wherein the stopper comprises an annular ring configured to compressibly engage an inner surface of the sidewall of the port.

An eighteenth aspect is a closure assembly of the sixteenth aspect, wherein the stopper comprises a plurality of annular rings configured to compressibly engage an inner surface of the sidewall of the port.

A nineteenth aspect is a closure assembly of any of aspects 8-16, wherein the sidewall comprises two or more gaps at a portion distal to the top, wherein a distal portion of the sidewall between the two gaps forms an extension that is resilient and outwardly deflectable.

A twentieth aspect is a closure assembly of the nineteenth aspect, wherein the inwardly annularly projecting element of the snap cap extends from the extension.

A twenty-first aspect is a cell culture system comprising the closure assembly of any of aspects 8-20.

Thus, embodiments of CLOSURE ASSEMBLY FOR CELL CULTURE APPARATUSES are disclosed. One skilled in the art will appreciate that the cell culture apparatuses and methods described herein can be practiced with embodiments other than those disclosed. The disclosed embodiments are presented for purposes of illustration and not limitation.

What is claimed is:

1. A closure assembly for a cell culture apparatus, comprising:
   a port having an annular sidewall defining a tapered lumen in communication with a cell culture chamber of the cell culture apparatus,
   wherein the tapered lumen has a larger inner diameter in proximity to an external opening and a smaller inner diameter in proximity to the cell culture chamber,
   wherein the sidewall comprises (i) external threads for cooperating with internal threads of a cap and (ii) an annularly protruding snap cap engagement feature; and
   a stopper configured to be received by the lumen of the port and configured to sealingly engage to the port, wherein the stopper comprises an annular flange having an outer diameter greater than an inner diameter of the lumen of the port at a surface of the port to which the stopper is configured to engage, wherein the stopper further comprises an extension portion configured to remain external to the port and to extend from the port, the extension portion defining a lumen configured to receive tubing; and
   a snap cap having a top and an annular sidewall extending from the top, wherein the sidewall of the snap cap comprises an inwardly annularly projecting element configured to engage with the annularly protruding snap cap engagement feature of the port wherein the top of the snap cap has a bottom surface that engages with and compresses the flange of the stopper against the surface of the port to which the stopper is configured to sealingly engage when the snap cap is fully engaged with the port, and wherein the top of the snap cap defines an opening through which the extension portion of the stopper is configured to project.

2. The closure assembly of claim 1, wherein the annularly protruding snap cap engagement feature of the port defines a largest outer diameter greater than the largest outer diameter defined by the external threads of the port.

3. The closure assembly of claim 1, wherein the annularly protruding snap cap engagement feature is positioned along the sidewall at a location more proximal to the cell culture chamber than the external threads.

4. The closure assembly of claim 1, wherein the stopper comprises an annular ring configured to compressibly engage an inner surface of the sidewall of the port.

* * * * *

UNITED STATES PATENT AND TRADEMARK OFFICE
CERTIFICATE OF CORRECTION

PATENT NO. : 10,100,273 B2  
APPLICATION NO. : 13/298679  
DATED : October 16, 2018  
INVENTOR(S) : Adam J Bear et al.

Page 1 of 1

It is certified that error appears in the above-identified patent and that said Letters Patent is hereby corrected as shown below:

On the Title Page

Column 2, item (56), other publications, Line 2, delete "Suppplementary" and insert
-- Supplementary --, therefor.

Signed and Sealed this
Nineteenth Day of May, 2020

Andrei Iancu
*Director of the United States Patent and Trademark Office*